(12) United States Patent
Lin et al.

(10) Patent No.: US 7,381,414 B2
(45) Date of Patent: Jun. 3, 2008

(54) MYCOPLASMA VACCINE, METHOD OF MAKING, AND APPLICATION THEREOF

(75) Inventors: Jiunn Horng Lin, Miaoli County (TW); Chung Nan Weng, Taipei (TW)

(73) Assignee: Animal Technology Institute Taiwan, Miaoli (TW)

( * ) Notice: Subject to any disclaimer, the term of this patent is extended or adjusted under 35 U.S.C. 154(b) by 0 days.

(21) Appl. No.: 10/869,084

(22) Filed: Jun. 17, 2004

(65) Prior Publication Data

US 2005/0037027 A1  Feb. 17, 2005

(30) Foreign Application Priority Data

Jun. 20, 2003 (TW) ............................... 92116884 A

(51) Int. Cl.
*A61K 39/02* (2006.01)
*A61K 39/00* (2006.01)
*A61K 39/116* (2006.01)

(52) U.S. Cl. ............................. 424/264.1; 424/234.1; 424/184.1; 424/203.1

(58) Field of Classification Search ............. 424/264.1, 424/278.1, 184.1, 234.1, 7.1, 203.1
See application file for complete search history.

(56) References Cited

U.S. PATENT DOCUMENTS 6,585,981 B1 * 7/2003 Pijoan ..................... 424/264.1

2003/0017171 A1 * 1/2003 Chu et al. ................ 424/201.1

OTHER PUBLICATIONS

Stoianov (Experiments to obtain and test vaccines against enzootic pneumonia in swine, Vet Med Nauki, 1976; 13(9): 24-7); abstract only, translation forthcoming.*
Heitmann et al (Studies on the transmission of mycoplasma from dam to fetus in the pig, Zentralblatt fuer Veterinaermedizin Reihe B, 1981; 28(5): 378-385) abstract only, translation is forthcoming.*
Rosengarten et al (Host-pathogen interactions in mycoplasma pathogenesis: virulence and survival strategies of minimalist prokaryotes, International Journal of Medical Microbiology, 2000; 290(1): 15-25) Abstract only.*
Jordan (Impediments to the development of additional vaccines: vaccines against important diseases that will not be available in the next decade, Reviews of infectious diseases, 1898, 11 supple 3: S603-12) Abstract only.*
Ellis, R (New Technologies for Making Vaccines, text book, 1998, 568-575).*
Stoyanov (Experiments to obtain vaccines against enzootic pneumonia in pigs, Veterinary Science 1976; 13(9): 24-7).*

* cited by examiner

*Primary Examiner*—Shanon Foley
*Assistant Examiner*—Lakia J Tongue
(74) *Attorney, Agent, or Firm*—Bacon & Thomas PLLC

(57) ABSTRACT

The present invention provides a mycoplasma vaccine, its preparation and application thereof. The foregoing mycoplasma vaccine comprises inactivated *Mycoplasma hyorhinis* ATIT-7 only or the mixture of inactivated *Mycoplasma hyorhinis* ATIT-7 and inactivated *Mycoplasma hyopneumoniae*, which effectively prevents the infection of swine enzootic pneumonia in pigs.

3 Claims, 3 Drawing Sheets

MYCOPLASMA VACCINE, METHOD OF MAKING, AND APPLICATION THEREOF

BACKGROUND OF THE INVENTION

1. Field of the Invention

The present invention relates to a vaccine prepared from *Mycoplasma hyorhinis* isolated from the lung lesions of pigs infected with enzootic pneumonia and the application of the foregoing vaccine.

2. Description of Related Art

Swine enzootic pneumonia is a chronic disease characterized by high infection rate and low mortality that infects 25~93% of swine herds and is positive in 28~80% of lung tissues of carcasses. The growth efficiency of infected pigs is reduced by 14~16%. In high-density rearing environment that is poorly ventilated and moist with wildly changing climate, the incidence and spread of swine enzootic pneumonia can rise to an alarming level, resulting in lower feed conversion, regarded growth, inflammatory reaction and immunosuppression in pigs. This disease is often accompanied by secondary infection of opportunistic pathogens, such as *Actinobacillus pleuropneumoniae, Pasteurella*, and *Streptococcus suis*, leading to serious economic loss and becoming one of important reasons for the cost increase of the pig industry.

The strategic approach to the prevention of swine enzootic pneumonia in Taiwan is to add antibiotic in the feed. But long-term use of antibiotic is prone to produce resistant strains and leads to the problem of residual antibiotic in the meat products, which poses significant health issue. Field experience also shows the preventive effect of feeding animals with drugs is not as ideal as expected.

There are three commonly seen mycoplasma in pigs, which are *Mycoplasma hyopneumoniae* (*M. hyopneumoniae*), *Mycoplasma hyorhinis* (*M. hyorhinis*), and *M. flocculate*. *M. hyopneumoniae* is the important causative organism of swine enzootic pneumonia (SEP); *M. hyorhinis* is the etiological agent of polyserositis and arthritis; *M. flocculate* has not been shown to cause diseases. In the past, all SEP incidences were caused by *M. hyopneumoniae*. But recently it is found that such disease is caused by either *M. hyorhinis* alone or the combination of *M. hyorhinis* and *M. hyopneumoniae*. In Taiwan, mycoplasma isolated from the lung lesions of pigs infected with SEP was only *M. hyopneumoniae* prior to 1996. In the case reports in other countries, *M. hyorhinis* was primarily isolated from the synovial fluid of pigs infected with arthritis, which did not cause SEP and was not considered an important pathogen for swine diseases. Taiwan never isolated this pathogen in the past. But starting in 1996, the *Mycoplasma* Laboratory of Animal Technology Institute Taiwan finds *mycoplasma* isolated from the lung lesions of pneumonia-infected pigs to be *M. hyorhinis* in more incidences as confirmed by antibody binding reaction using Western blotting and comparison with ATCC standard strains.

The Animal Technology Institute Taiwan provides *mycoplasma* isolation and identification service to pig farms around the country, and sees higher and higher incidence of *M. hyorhinis* isolates from pneumonia cases. In the 242 cases in 2001 and 205 cases in 2002, the *M. hyopneumoniae* infection rate dropped from 46.8% in 2001 to 15.8% in 2002, while that of *M. hyorhinis* rose from 65.5% in 2001 to 79.2% in 2002. The infection rate of the mixture of *M. hyopneumoniae* and *M. hyorhinis* was 14.4% in 2001 and 15% in 2002. These figures indicate rapidly rising *M. hyorhinis* infection in swine pneumonia cases in Taiwan and rapidly dropping infection rate of *M. hyopneumoniae*, while infection rate of the mixture of the two remains steady. It also indicates that *M. hyorhinis* is gradually replacing *M. hyopneumoniae* as the most significant pathogen of SEP. The past belief was that *M. hyopneumoniae* was the only species among mycoplasma to cause SEP. This is not the situation now. In the isolation cases described above, there was one pure *M. hyorhinis* infection case in 2001, and five such cases in 2002, suggesting *M. hyorhinis* alone could elicit SEP.

Field experience shows that the chance of reinfection with the same *mycoplasma* species is relatively low, indicating good innate immunity of the pigs against such pathogen. Thus using vaccination as a means of disease prevention is a viable approach. Given the weak cross reaction between the antigens of *M. hyorhinis* and *M. hyopneumoniae*, it is found in pig farm survey on vaccination that pigs administered with *M. hyopneumoniae* vaccine were not effectively protected against the infection of *M. hyorhinis*. For pigs infected with both *mycoplasma* species, the effect of administering *M. hyopneumoniae* vaccine or *M. hyorhinis* vaccine alone was not satisfactory. Only vaccine containing the mixture of both mycoplasma antigens provides adequate protection. Thus developing vaccine containing *M. hyorhinis* or both *M. hyorhinis* and *M. hyopneumoniae* is a pressing task.

SUMMARY OF THE INVENTION

For the prevention of swine enzootic pneumonia, the present invention provides a *mycoplasma* vaccine, comprising at least an effective amount of inactivated *M. hyorhinis* ATIT-7. The foregoing *M. hyorhinis* has been preserved at the Culture Collection and Research Center of the Food Industry Research and Development Institute (No. BCRC910223) since May 8, 2003. This isolate was also deposited in the American Type Culture Collection (ATCC, 10801 University Blvd., Manassas, Va. 20110-2209, USA) under the Budapest Treaty on Jun. 9, 2006, and was given the ATCC Accession No. PTA-7651. Besides containing *M. hyorhinis* ATIT-7, the foregoing *mycoplasma* vaccine may further include an effective amount of inactivated *M. hyopneumoniae*, wherein the concentration of *M. hyopneumoniae* in the vaccine is 60~80% v/v and that of *M. hyorhinis* ATIT-7 is 40~20% v/v.

The *mycoplasma* vaccine may further contain an adjuvant or diluent, wherein the inactivated *mycoplasma* fluid (containing only *M. hyorhinis* ATIT-7 or the mixture of *M. hyorhinis* ATIT-7 and *M. hyopneumoniae*) comprises 50~75% v/v of the vaccine composition, and the adjuvant comprises 50~25% v/v.

The *mycoplasma* vaccine may be administered subcutaneously or intramuscularly to the animal.

The *M. hyorhinis* ATIT-7 is cultured until its $O.D._{550}$ reaches the level of 0.14 to 0.33, and *M. hyopneumoniae* is cultured until its $O.D._{550}$ reaches the level of 0.08 to 0.16.

The present invention also relates to a method for the preparation of *mycoplasma* vaccine, comprising the steps of: culturing *M. hyorhinis* ATIT-7 in vaccine culture medium; inactivating the harvested *M. hyorhinis* ATIT-7 with formalin; and letting the culture stand under 2-8° C. to continue the inactivation for 16 to 72 hours. *M. hyorhinis* ATIT-7 is cultured until its $O.D._{550}$ reaches the level of 0.14 to 0.33 with viable count of higher than $10^9$ CCU/mL. The concentration of said formalin is preferably between 0.1 and 0.5%, and more preferably between 0.1 to 0.2%.

The vaccine culture medium for cultivating *M. hyorhinis* comprises 500 ml of Hank's solution, 12,000 ml of distilled water, 82 g of Bacto brain heart infusion (Difco), 87 g of Bacto PPLO broth, 600 ml of yeast extract, 45 ml of phenol red, 2.5 g of bacitracin, 2.5 g of penicillin or methicillin, and 1,500 to 5,000 g of inactivated porcine serum or inactivated horse serum.

The method for preparing *M. hyorhinis* vaccine can further contain the steps of: culturing *M. hyopneumoniae* in a vaccine culture medium; inactivating harvested culture fluid with formalin; and letting the culture stand under 2-8° C. to continue the inactivation for 16 to 72 hours; admixing the resulting inactivated *M. hyopneumoniae* with aforesaid inactivated *M. hyorhinis*. The concentration of said formalin is preferably between 0.1 and 0.5%, more preferably between 0.1 to 0.2%. *M. hyopneumoniae* is cultured until its $O.D._{550}$ reaches the level of 0.08 to 0.16 with viable count of higher than $10^9$ CCU/mL.

The vaccine culture medium for cultivating *M. hyopneumoniae* comprises 500 ml of Hank's solution, 12,000 ml of distilled water, 82 g of Bacto brain heart infusion (Difco), 87 g of Bacto PPLO broth, 600 ml of yeast extract, 45 ml of phenol red, 2.5 g of bacitracin, 2.5 g of penicillin or methicillin, and 1,500 to 5,000 g of inactivated porcine serum.

The present invention further provides a pharmaceutical composition for the prevention of *mycoplasma* infection, comprising an effective amount of the aforesaid *mycoplasma* vaccine and a pharmaceutically acceptable carrier.

The present invention also relates to a *M. hyorhinis* strain ATIT-7 capable of infecting swine and causing pneumonia, wherein said strain has been preserved at the Culture Collection and Research Center of the Food Industry Research and Development Institute (No. BCRC 910223) since May 8, 2003.

The present invention also provides a strain collection method, comprising the steps of: isolating *M. hyorhinis* strain ATIT-7 from the lung lesions of pigs infected with pneumonia; culturing said strain in culture medium under 35~38° C. for 16 to 24 hours to obtain viable organism count of higher than $10^9$ CCU/mL. The culture medium for cultivating *M. hyopneumoniae* comprises 500 ml of Hank's solution, 12,000 ml of distilled water, 82 g of Bacto brain heart infusion (Difco), 87 g of Bacto PPLO broth, 600 ml of yeast extract, 45 ml of phenol red, 2.5 g of bacitracin, 2.5 g of penicillin or methicillin, and 1,500 to 5,000 g of inactivated porcine serum or inactivated horse serum.

The *M. hyorhinis* strain ATIT-7 has been preserved at the Culture Collection and Research Center of the Food Industry Research and Development Institute (No. BCRC 910223) since May 8, 2003.

DETAILED DESCRIPTION OF THE INVENTION

Figure 1:
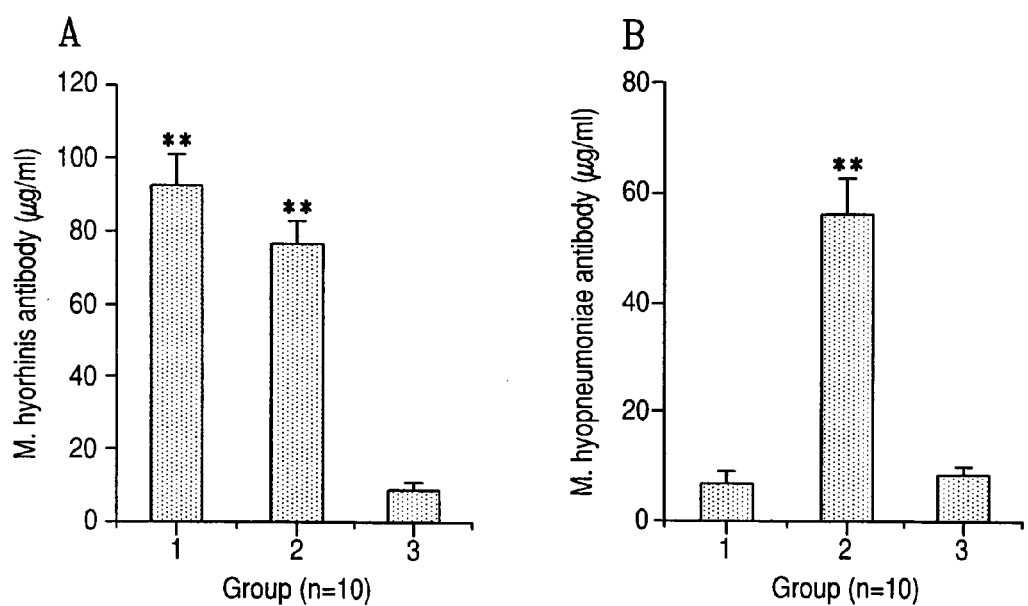
FIG. 1A shows the production of *M. hyorhinis* antibody in mice vaccinated with *M. hyorhinis* bacterin and bacterin containing the mixture of *M. hyorhinis* and *M. hyopneumoniae*.
FIG. 1B shows the production of *M. hyopneumoniae* antibody in mice vaccinated with *M. hyorhinis* bacterin and bacterin containing the mixture of *M. hyorhinis* and *M. hyopneumoniae*.

The features and advantages of the present invention are further depicted with the illustration of examples.

EXAMPLE

Preparation of Vaccine

1. Vaccine Strain

PRIT-5 is a *M. hyopneumoniae* strain disclosed in another Taiwanese patent of the applicant filed on Apr. 24, 1990 and approved on Apr. 21, 1991. PRIT-5 strain has been preserved at the Culture Collection and Research Center of the Food Industry Research and Development Institute (No. CCRC910045) since Mar. 14, 1996. ATIT-7 is a *M. hyorhinis* strain isolated from lung lesions of infected pigs, which is found to proliferate very fast in culture medium; its viable count could reach over $10^9$ CCU/mL after growing in culture medium under 35~38° C. for 16 hours, while the count of other *M. hyorhinis* strains fell in the range of $10^8$~$10^9$ CCU/mL. The ATIT-7 strain has been preserved at the Culture Collection and Research Center of the Food Industry Research and Development Institute (No. BCRC910223) since May 8, 2003.

2. Preparation of Culture Medium

The culture medium for preparing the vaccine is formulated as follows:

| | |
|---|---|
| Hank's solution | 500 ml |
| Distilled water | 12,000 ml |
| Bacto brain heart infusion | 82 g |
| Bacto PPLO broth | 87 g |
| Yeast extract | 600 ml |
| Phenol red | 45 ml |
| Bacitracin | 2.5 g |
| Penicillin or methicillin | 2.5 g |
| Porcine serum | 1,500 to 5,000 g |

(The porcine serum is first inactivated under 56° C. for 30 minutes one to two times)

The formulated culture medium has pH adjusted to 7.4~7.6 and is then filtered with 0.2 μm Millipore.

3. Preparation of Vaccine

Culture and Treatment of *M. Hyorhinis* Vaccine

Let *M. hyorhinis* strain ATIT-7 grow in vaccine culture medium which is placed in 37° C. shaking incubator for 8-24 hours. Harvest the culture when the bacterial fluid turns yellow. Use photoelectric colorimeter to measure the $O.D._{550}$, which must reach 0.14 to 0.33, and the viable-organism count which must be higher than $10^9$ CCU/mL.

Add 0.1 to 0.2% formalin to the harvested culture. After carrying out inactivation in 37° C. shaking incubator for 1 hour, place the bacterial fluid under 2~8° C. to continue inactivation for 16 to 72 hours. Mix the formalin-treated bacterial fluid with adjuvant (50~75% v/v of bacterial fluid and 50~25% v/v of formalin). Agitate the mixture with agitator for 15 minutes. The resulting vaccine is stocked under 4° C. for future use. Each dose of the vaccine is 2 ml with each ml containing about $2 \times 10^9 \sim 2 \times 10^{10}$ CCU.

Culture and Treatment of *M. Hyorhinis* and Mixture Vaccine

Let strain PRIT-5 and ATIT-7 grow in vaccine culture medium which is placed in 37° C. shaking incubator for 36-72 hours (PRIT-5) and 8-24 hours (ATIT-7) respectively. Harvest the culture when the bacterial fluid turns yellow. Use photoelectric colorimeter for measurement. The $O.D._{550}$ of PRIT-5 must reach 0.08 to 0.16, and its viable-organism count must be higher than $10^9$ CCU/mL; The $O.D._{550}$ of ATIT-7 must reach 0.14 to 0.33, and its viable-organism count must be higher than $10^9$ CCU/mL.

Add 0.1 to 0.2% formalin to the harvested ATIT-7 and PRIT-5 cultures respectively. After carrying out inactivation in 37° C. shaking incubator for 1 hour, place the bacterial fluid under 2~8° C. to continue inactivation for 16 to 72 hours. Admix the formalin-treated ATIT-7 bacterin and formalin-treated PRIT-5 bacterin by the respective ratio of 40~20% v/v and 60~80% v/v into a bacterin mixture.

Admix the bacterin mixture with adjuvant (50~75% v/v of bacterin mixture and 50~25% v/v of formalin). Agitate the mixture with agitator for 15 minutes. Each dose of the resulting vaccine is 2 ml with each ml containing about $2 \times 10^9 \sim 2 \times 10^{10}$ CCU.

4. Use of Vaccine

Each piglet was given two or three intramuscular injections of the prepared vaccine at one dose each time. The first dose was administered at 1-3 weeks of age; the second dose was administered at 3-5 weeks of age; the third dose was administered at 5-7 weeks of age. The vaccine must be mixed well prior to use.

5. Vaccine Safety Test (1) Safety test in mice: Obtain 40 BALB/c mice. Randomly assign 8 mice as control group and divide the remaining 32 mice into 4 test groups with 8 mice in each group. Group 1 were subcutaneously inoculated with 0.5 ml *M. hyorhinis* vaccine; Group 2 was subcutaneously inoculated with 0.5 ml mixture vaccine (mixture of *M. hyorhinis* and *M. hyopneumoniae* bacterins); Group 3 received intraperitoneal inoculation of 0.5 ml *M. hyorhinis* vaccine; and Group 4 received intraperitoneal inoculation of 0.5 ml mixture vaccine. The mice were observed for 14 days after vaccination. All mice survived and no adverse reaction was observed.

(2) Safety test in piglets: Pick 15 one-week old piglets. Randomly divide the piglets into 5 groups with 3 heads per group. Group 1 was administered with one dose of *M. hyorhinis* vaccine intramuscularly on the side of neck; Group 2 received 5 doses of *M. hyorhinis* vaccine intramuscularly on the side of neck; Group 3 was vaccinated with 1 dose of mixture vaccine intramuscularly on the side of neck; and Group 4 received 5 doses of mixture vaccine intramuscularly on the side of neck. All piglets survived and no adverse reaction was observed in subsequent 14 days of observation period.

6. Vaccine Efficacy Test (1) Antibody titer assay in mice: Obtain 30 four-week old BALB/c female mice. Randomly divide them into 3 groups with 10 mice in each group. Group 1 and Group 2 were subcutaneously vaccinated twice with *M. hyorhinis* vaccine and mixture vaccine respectively. Group 3 was the control group. In one week after the second vaccination, blood was collected from eye orbit under anesthesia. The collected blood was placed under room temperature for 1 hour and then placed under 4° C. overnight. The blood was then centrifuged under 1107×g for 30 minutes. After centrifugation, supernatant was removed, placed in a new centrifuge tube, and then subject to ELISA immunoassay. The results are as shown in FIG. 1. FIG. 1A shows the level of *M. hyorhinis* antibody produced in mice vaccinated with *M. hyorhinis* vaccine (Group 1) and mixture vaccine (Group 2); FIG. 1B shows the level of *M. hyopneumoniae* antibody in mice vaccinated with mixture vaccine (Group 2). It is clear that two administrations of *M. hyorhinis* vaccine or *M. hyorhinis*-*M. hyopneumoniae* mixture vaccine will boost the level of serum antibody and thus enhance the pig's immune reaction.

Figure 2:
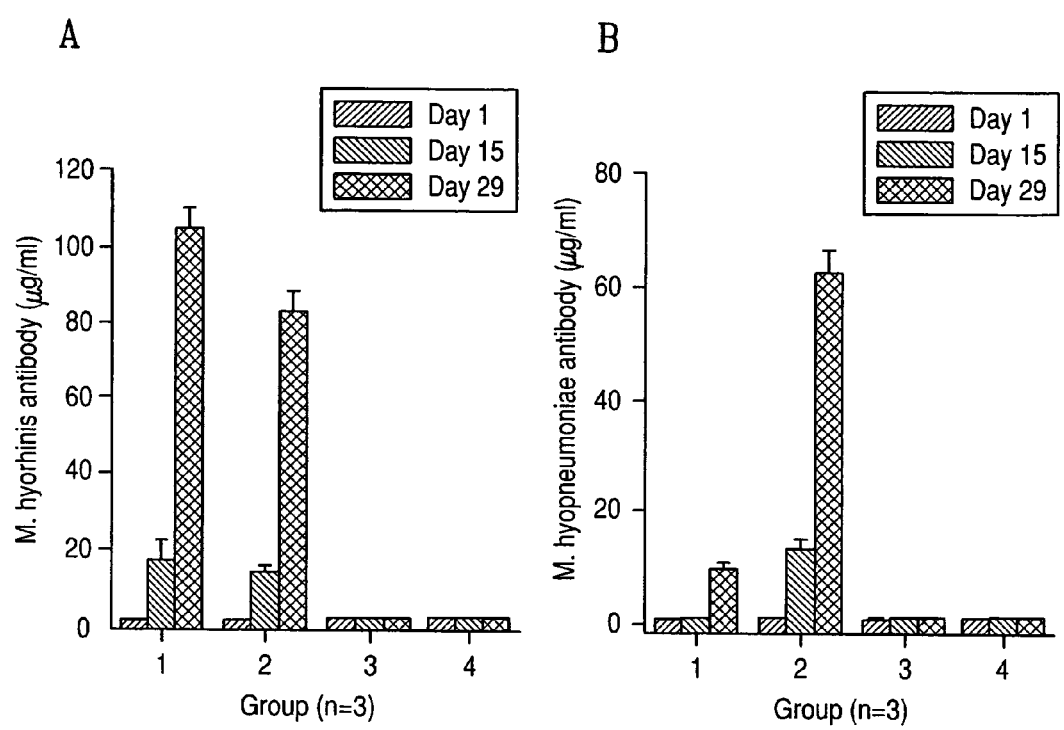
FIG. 2A shows the production of *M. hyorhinis* antibody in piglets vaccinated with *M. hyorhinis* bacterin and bacterin containing the mixture of *M. hyorhinis* and *M. hyopneumoniae* on days 1, 15, and day 29 respectively.
FIG. 2B shows the production of *M. hyopneumoniae* antibody in piglets vaccinated with *M. hyorhinis* bacterin and bacterin containing the mixture of *M. hyorhinis* and *M. hyopneumoniae* on days 1, 15, and day 29 respectively.
Figure 3:
FIG. 3A-D observes the pathological changes of the lungs of piglets following immunoresistance test, in which A, B, C, D represents Group 1, 2, 3, and 4 respectively; Group 1 was vaccinated with *M. hyorhinis* bacterin and challenged with virulent *M. hyorhinis*; Group 2 was vaccinated with *M. hyorhinis*+*M. hyopneumoniae* bacterin and challenged with virulent *M. hyorhinis* and *M. hyopneumoniae*; Group 3 was not vaccinated but challenged with virulent *M. hyorhinis*; and Group 4 was not vaccinated and not challenged with *mycoplasma*.

(2) Immunoresistance test in piglets: The purpose of resistance test is to compare the immunity of vaccinated and non-vaccinated piglets against *mycoplasma* infection. Obtain 12 3-week old piglets which were divided into 4 groups with 3 heads each. Group 1 was vaccinated with *M. hyorhinis* vaccine and then challenged with virulent *M. hyorhinis*; Group 2 was administered with mixture vaccine and then challenged with virulent *M. hyorhinis* and *M. hyopneumoniae*; Group 3 (control group) was given PBS and challenged with virulent *M. hyorhinis*; and Group 4 (control group) was given PBS and challenged with PBS instead of virulent *mycoplasma* (see Table 1). The first vaccination was given on day 1, the booster shot was given on day 15, and the challenge was carried out on day 29. The piglets were sacrificed on day 50. Blood was collected three times prior to vaccination and challenge on days 1, 15, and 29 respectively, and then subjected to ELISA immunoassay. The results are as shown in FIG. 2. FIG. 2A shows that *M. hyorhinis* serum antibody was observed in both Group 1 and Group 2, and the antibody level peaked after the second vaccination (day 29). FIG. 2B shows the presence of *M. hyopneumoniae* serum antibody in Group 2 piglets vaccinated with mixture vaccine. Both graphs indicate rising *mycoplasma* serum antibodies in vaccinated piglets. After two doses of vaccines, Group 1 and Group 3 were challenged with virulent *M. hyorhinis*, while Group 2 was challenged with both virulent *M. hyorhinis* and *M. hyopneumoniae*, and Group 4 was challenged with PBS in place of *mycoplasma* as control. In three weeks after the challenge, the piglets were weighed and then euthanized and necropsied. The pathological changes of the lungs of necropsied piglets are shown in FIG. 3. FIG. 3A shows the lung from Group 1, FIG. 3B shows the lung from Group 2, and so on. The harvested lungs had lesion count and microorganism isolation with results depicted in Table 2. The average body weight of the vaccinated group and non-vaccinated group differed by nearly 15 kg, suggesting *M. hyorhinis* infection significantly retarded the growth of pigs, while the vaccinated groups were not affected. Based on the observation of lung lesions in FIG. 3 and lung lesion count as depicted in Table 2, it is found that the lungs of vaccinated groups and non-challenged group (Group 4, FIG. 3D) did not have lesions, while non-vaccinated and challenged group (Group 3, FIG. 3C) showed typical *mycoplasma* pneumonia lesion (at where black arrow is pointed at) with striking difference between the two.

TABLE 1

Vaccine Efficacy Test Design

| Group | No. of piglets vaccinated | Day 1 vaccination | Day 15 vaccination | Day 29 challenge | Day 50 necropsy |
|---|---|---|---|---|---|
| 1 | 3 | M. hyorhinis | M. hyorhinis | M. hyorhinis | — |
| 2 | 3 | M. hyorhinis + M. hyopneumoniae | M. hyorhinis + M. hyopneumoniae | M. hyorhinis + M. hyopneumoniae | — |
| 3 | 3 | PBS | PBS | M. hyorhinis | — |
| 4 | 3 | PBS | PBS | PBS | — |

TABLE 2

Post-challenge Growth, Lung Lesion Count and M. hyopneumoniae isolation

| Group | Body weight (kg) | | | Lung lesion count | Mycoplasma isolation |
|---|---|---|---|---|---|
| | Before vaccination | Before challenge | Before necropsy | | |
| 1 | 4.3 ± 0.1 | 15.1 ± 0.5 | 37.2 ± 3.4 | 0 | 0/3 |
| 2 | 4.4 ± 0.2 | 14.9 ± 0.3 | 39.8 ± 1.5 | 0 | 2/3 |
| 3 | 4.0 ± 0.2 | 13.8 ± 0.3 | 24.1 ± 2.3 | 7.3 ± 5.0 | 2/3 |
| 4 | 3.9 ± 0.2 | 14.2 ± 0.3 | 34.2 ± 1.6 | 0 | 0/3 |

(3) Field test: To understand the ability of vaccine of the present invention to elicit protective immunity in the field, vaccines were provided to two pig farms; one had incidence of simple M. hyorhinis infection (herds of 1,300 pigs), and the other had incidence of M. hyorhinis and M. hyopneumoniae mixed infection (herds of 4,000 pigs). After vaccination, the pig farm that had simple M. hyorhinis infection saw the number of piglet death drop from 137 heads to 50 heads and the herds survival rate rising from 89% to 96%; the pig farm that had mixed infection saw the number of piglet death drop from 525 heads to 75 heads, and the herds survival rate rising from 86% to 98%.

The embodiment of the present invention as disclosed above is not meant to limit this invention. All modifications and alterations made by those familiar with the skill without departing from the spirits of the invention and appended claims shall remain within the protected scope and claims of the invention.

What is claimed is:

1. A *Mycoplasma* vaccine composition for the prevention of swine enzootic pneumonia, comprising two components: a *Mycoplasma* component comprising 50 to 75% v/v of the vaccine composition and an adjuvant component comprising 25 to 50% v/v of the vaccine composition, wherein the *Mycoplasma* component comprises 60 to 80% v/v of inactivated *Mycoplasma hyopnuemoniae* and 20 to 40% of inactivated *Mycoplasma hyorhinis* ATAIT-7 deposited with American Type Culture Collection under the accession number ATCC PTA-7651.

2. The mycoplasma vaccine according to claim 1, wherein said vaccine is administered to animals via subcutaneous or intramuscular route.

3. A pharmaceutical composition for the prevention of mycoplasma infection, comprising an effective amount of mycoplasma vaccine of claim 1 and a pharmaceutically acceptable carrier.

* * * * *